(12) United States Patent
Drager (10) Patent No.: US 7,666,133 B2
(45) Date of Patent: Feb. 23, 2010

(54) APPARATUS AND METHOD FOR CORRECTING URINARY INCONTINENCE

(75) Inventor: Sam Drager, 1455 Crusade Dr., Copley, OH (US) 44321

(73) Assignee: Sam Drager, Copley, OH (US)

( * ) Notice: Subject to any disclaimer, the term of this patent is extended or adjusted under 35 U.S.C. 154(b) by 682 days.

(21) Appl. No.: 11/164,629

(22) Filed: Nov. 30, 2005

(65) Prior Publication Data

US 2006/0195009 A1 Aug. 31, 2006

Related U.S. Application Data

(60) Provisional application No. 60/633,312, filed on Dec. 6, 2004.

(51) Int. Cl.
*A61F 2/02* (2006.01)
(52) U.S. Cl. .............................. 600/29; 600/30; 604/8; 604/93.01; 606/108
(58) Field of Classification Search .................. 600/29, 600/30, 31, 32; 251/83, 294; 137/522, 523
See application file for complete search history.

(56) References Cited

U.S. PATENT DOCUMENTS

| | | | |
|---|---|---|---|
| 3,953,897 A | 5/1976 | Chevallet et al. | |
| 4,344,435 A * | 8/1982 | Aubin | 604/246 |
| 4,427,177 A * | 1/1984 | Constantinescu et al. | 251/230 |
| 4,553,271 A | 11/1985 | Baker | |
| 4,619,245 A | 10/1986 | Haber et al. | |
| 4,679,546 A | 7/1987 | van Waalwijk van Doorn et al. | |
| 4,976,735 A * | 12/1990 | Griffith et al. | 623/23.65 |
| 5,030,199 A | 7/1991 | Barwick et al. | |
| 5,108,430 A * | 4/1992 | Ravo | 623/23.68 |
| 5,140,999 A | 8/1992 | Ardito | |
| 5,509,888 A | 4/1996 | Miller | |
| 5,795,288 A | 8/1998 | Cohen et al. | |
| 5,902,337 A | 5/1999 | Di Lelio et al. | |
| 6,053,064 A * | 4/2000 | Gowing et al. | 74/89.45 |
| 6,053,935 A * | 4/2000 | Brenneman et al. | 606/232 |
| 6,063,119 A | 5/2000 | Pintauro et al. | |
| 6,105,580 A * | 8/2000 | Von Iderstein et al. | 128/885 |
| 6,132,365 A | 10/2000 | Sigurdsson | |
| 6,319,191 B1 | 11/2001 | Sayet et al. | |
| 6,406,423 B1 | 6/2002 | Scetbon | |
| 6,409,656 B1 | 6/2002 | Sangouard et al. | |

(Continued)

OTHER PUBLICATIONS

National Association for Continence (NAFC), www.nafc.org, Resource Guide—Products and Services for Incontinence "Surgical Devices / Implantables / Treatments", pp. 42-43.

(Continued)

*Primary Examiner*—Charles A Marmor, II
*Assistant Examiner*—Catherine E Burk (57) ABSTRACT

An apparatus and a method for urine containment, storage, and release is provided for male and female patients suffering from incontinence. The device comprises a housing including a valve implanted generally in the bladder of a male or female patient. The device further comprises an access port connecting the housing and extending through the abdominal wall of the abdomen. The device replaces the functionality of the urethral valve and allows on demand drainage of the natural bladder which flows from the natural bladder into the urethra and exits the body. The access ports may provide a backup system for urine drainage as well as facilitate access to the gastro-intestinal region as well as the rest of the body.

13 Claims, 6 Drawing Sheets

U.S. PATENT DOCUMENTS

| | | |
|---|---|---|
| 6,443,886 B2 | 9/2002 | Deininger et al. |
| 6,527,702 B2 | 3/2003 | Whalen et al. |
| 6,551,235 B2 | 4/2003 | Forsell |
| 6,558,370 B2 | 5/2003 | Moser |
| 6,579,225 B2 | 6/2003 | Pregenzer et al. |
| 6,638,208 B1 | 10/2003 | Natarajan et al. |
| 6,659,937 B2 | 12/2003 | Polsky et al. |
| 6,746,489 B2 | 6/2004 | Dua et al. |
| 6,984,221 B1 * | 1/2006 | Scheye ................. 604/178 |
| 7,041,090 B2 * | 5/2006 | Bolmsjo et al. ........ 604/327 |
| 2002/0045868 A1 * | 4/2002 | Reever ................. 604/328 |
| 2005/0096751 A1 | 5/2005 | Gerber et al. |

OTHER PUBLICATIONS

Uromedica, "Introducing the post-operatively adjustable treatment for stress urinary incontinence" Internet printout Jan. 12, 2005, 2 pages.

\* cited by examiner

APPARATUS AND METHOD FOR CORRECTING URINARY INCONTINENCE

This application claims the benefit of U.S. provisional patent application Ser. No. 60/633,312, filed Dec. 6, 2004, herein incorporated by reference.

TECHNICAL FIELD

The invention relates to a device and method for correcting urinary incontinence, and more particularly, to a device having a valve that is at least partially inserted into the natural bladder of a patient and that also includes at least one access port extending from the housing a sufficient predetermined length to reach through the abdominal wall of the patient. The access port enables easy repair and maintenance of the valve device as well as providing an insertion location for catheters, cameras, medical instruments, etc., through the access port and into the natural bladder as well as other areas of the patient's body.

BACKGROUND OF THE ART

The urinary system helps to maintain proper water and salt balance throughout the body. The process of urination begins in the two kidneys, which process fluids and dissolved waste matter to produce urine. Urine flows out of the kidneys into the bladder through two long tubes called ureters. The bladder is a sac that acts as a reservoir for urine. It is covered with a membrane and enclosed in a powerful muscle called the detrusor. The bladder rests on top of the pelvic floor. This is a muscular structure similar to a sling running between the pubic bone in front to the base of the spine. The bladder stores the urine until it is eliminated from the body via a tube called the urethra, which is the lowest part of the urinary tract. (In men it is enclosed in the penis. In women it leads directly out.) The connection between the bladder and the urethra is called the bladder neck. Strong muscles called sphincter muscles encircle the bladder neck (the smooth internal sphincter muscles) and urethra (the fibrous external sphincter muscles).

The process of urination is a combination of automatic and conscious muscle actions. There are two phases: the emptying phase and the filling and storage phase. When a person has completed urination, the bladder is empty. This triggers the filling and storage phase, which includes both automatic and conscious actions.

An automatic signaling process in the brain uses a pathway of nerve cells and chemical messengers (neurotransmitters) called the cholinergic and adrenergic systems. The brain signals the detrusor muscle, which surrounds the bladder, to relax. As the muscles relax, the bladder expands and allows urine to flow into it from the kidneys. As the bladder fills to its capacity (about 8 to 16 oz of fluid) the nerves in the bladder send back signals of fullness to the spinal cord and the brain.

As the bladder swells, the person becomes conscious of a sensation of fullness. In response, the individual holds the urine back by voluntarily contracting the external sphincter muscles (the muscle group surrounding the urethra). (These are the muscles that children learn to control during the toilet training process.) When the need to urinate overcomes the conscious holding back, then urination (the emptying phase) begins. At the point when a person is ready to urinate, the nervous system initiates the voiding reflex. In this case, the nerves in the spinal cord (not the brain) trigger the event. These nerves signal the detrusor muscles around the bladder to contract. At the same time, nerves are also signaling the involuntary internal sphincter (a strong muscle encircling the bladder neck) to relax. With the bladder muscles squeezing and its neck open, the urine flows out of the bladder into the urethra. Once the urine enters the urethra a person consciously relaxes the external sphincter muscles, which allows urine to pass out. Urine is then completely drained from the bladder and the process of filling and storing begins again.

In a person with urinary incontinence (UI) the muscles, nerves, or both are no longer under that person's control. This presents the problem of controlling the release and containment of urine. UI affects all aspects of a person's life and may affect their health. Urinary incontinence is a problem estimated to afflict about 25 million people in the United States. The annual cost of providing care for persons with UI is estimated to be in excess of $16 billion. Urinary incontinence is one of the most common chronic medical conditions seen in primary care practice. UI is more prevalent than diabetes, Alzheimer's disease, and many other conditions that receive considerably more attention. Incontinence is an expensive problem, generating more costs each year than coronary artery bypass surgery and renal dialysis combined. Women have higher rates of urinary incontinence than men. Prevalence increases with age-one third of women older than 65 years have some degree of incontinence, and 12 percent have daily incontinence. A shift to a healthier, more active and older population and a society which is increasingly mobile is resulting in an increasing number of persons suffering from incontinence, and a demand from that population for more effective and reliable solutions for urinary incontinence.

Pharmaceutical companies have developed several new incontinence medications. Sales of these medications were predicted to measure billions of dollars in 2004. The market for adult absorbent devices or diapers alone is in excess of $2 billion and continues to grow. Total sales of products used in the diagnosis and treatment of UI were estimated at $1.37 billion in 2001. Due to the size of both current and potential UI markets, medical professionals and product manufacturers have placed significant emphasis on research into the diagnosis and treatment of this condition, which has resulted in the development of several new therapies and approaches that could potentially delay UI symptoms for years in some patients.

UI can affect persons of all ages, and may be the result of physical disability or a psychological condition. There are several different types of incontinence. Acute (or Transient) Incontinence is caused by generally treatable medical problems. Medical conditions such as dehydration, delirium, urinary retention, fecal impaction/constipation, and urinary tract infection; can cause an onset of UI. Additionally, certain medications can cause or contribute to an incontinence problem, such as anticholinergic agents, antihistamines, antidepressants (TCA), phenothiazines, disopyramides, opiates, antispasmodics, Parkinson drugs, alpha-adrenergic agents (high blood pressure drugs), sympathomimetics (decongestants), and sympatholytics (e.g., prazosin, terazosin, and doxazosin).

Chronic UI is conventionally classified into four groups: Stress, Urge, Overflow, and Functional incontinence. They may occur alone or in combination, the latter being more common as the patient ages. Chronic UI is persistent and more difficult problem to treat. Often, more than one type of incontinence is present. Approximately 40% of all incontinence cases fall into more than one of the four categories. A variety of disease and medical problems may contribute to each of the four major types of incontinence. Because incontinence is a symptom rather than a distinct disease, it is often difficult to determine a definite cause.

Stress incontinence is the involuntary leakage of small amounts of urine resulting from an increased pressure in the abdomen. Events which may result in such involuntary leakage include sneezing, coughing, laughing, bending, lifting, etc. While primarily a female problem, men also suffer from stress incontinence. Stress incontinence in men is typically the result of a weakened urethral sphincter that surrounds the urethra, frequently as a result of prostate surgery.

Urge incontinence, characterized by insufficient ability to prevent voiding once the urge to void arises, is most common in middle aged and older people. Detrunorm hyperreflexia or instability which is associated with disorders of the lower urinary tract or neurologic system is a common cause. However, urge incontinence can also be the result of urologic carcinoma, diverticula, or other physical abnormalities.

Overflow incontinence, which accounts for 10-15% of urinary incontinence, is usually the result of an obstruction (e.g., enlarged prostate, urethral stricture) of the bladder outlet or an atonic bladder as the result of neurologic injury (e.g., spinal chord trauma, stroke), diabetic neuropathic bladder, or drug-induced atonia. The obstruction leads to bladder overfilling, resulting in a compulsive detrusor contraction. In this form of UI chronic "dribbling" is common. Drug induced atonia can be caused by anti-cholinergics, narcotics, antidepressants, and smooth muscle relaxants.

Functional incontinence accounts for 25% of all incontinence. It occurs primarily when a person is confined and sedentary, such as in a nursing home or during a long period of convalescence. Functional incontinence is sometimes diagnosed as a result of the individual simply being unable to communicate his or her needs, or through other sensory impairments that make the individual unaware of his or her need to void. This condition can further result from decreased mental function, decreased functional status, and/or a simple unwillingness to physically go to the toilet.

UI, or even the fear of an incontinent incidence, can lead to discomfort and embarrassment, and eventually to social withdrawal and isolation. Normal activities, social interaction, and sexual activity are often curtailed or avoided as a result. UI is the predominant reason aging parents are put into nursing homes. Urinary incontinence is a chronic (long-term) problem.

The current protocols for treating urinary incontinence from least to most invasive are education and behavior therapy, pelvic floor muscle exercises, absorbent pads, external devices, medication, non-surgical implants, surgery procedures, and surgical implants. Pelvic muscle training exercises called Kegel exercises are primarily used to treat people with stress incontinence. However, these exercises may also be beneficial in relieving the symptoms of urge incontinence. The principle behind Kegel exercises is to strengthen the muscles of the pelvic floor, thereby improving the urethral sphincter function. The success of Kegel exercises depends on proper technique and adherence to a regular exercise program. Minimally invasive therapies can lead to improvement in incontinence but not necessarily a cure. Improvement generally does not occur overnight. Patients need time to adapt to behavioral changes. Results with pelvic floor exercises may typically take three to six months.

Diapers and other absorbent constructions are the most popular remedy because they are easily obtained, and can address acute UI symptoms quickly. However, while affording reasonably effective control of urine leakage and providing mobility to the patient, absorbents also have very serious drawbacks. A major deficiency is that urine is not removed from the genital region. The absorbents merely collect and disperse the urine and maintain a moist environment with the urine typically remaining in contact with skin surfaces, causing irritation and discomfort. While improved constructions with different absorbent layers attempt to direct the urine to a region away from the skin and minimize contact, the resulting benefit is less then desired. Absorbent devices also require a large area of absorbent material surrounded by water proof external barriers, usually in the form of pants or diapers. Such an arrangement when dry is uncomfortable to the wearer. When wet the discomfort level increases greatly and the wearer must deal with the distinctive, embarrassing odor of urine. Once removed, whether soiled or not, the disposable-type diaper usually must be disposed of, creating the need to always carry a supply of such absorbent devices.

Incontinence treated by catheterization, use of absorbent products, and for males, devices attached to the exterior surface of the penis to collect urine discharge have many disadvantages. Catheterization, whether intermittent or permanent, is an unacceptable approach in many instances and is the least preferred type of bladder management. The procedure is very inconvenient and many patients are psychologically averse to self-catheterization, or physically unable to perform the manipulations required. Catheters need to be changed frequently. A major deficiency of either permanent or intermittent catheterization is that the urine of virtually every patient becomes contaminated by bacteria. Catheter-associated bacteria represent the most common infection acquired in acute care and long-term care facilities. Complications ranging from bladder spasms and catheter leakage to death caused by septicemia are also well known limitations. Bacterial entry into the bladder occurs either from extra luminal migration along the outside of the catheter, contamination on insertion of the catheter, or contamination of the drainage bag, leading to bacterial growth and subsequent migration into the bladder.

Pharmaceutical companies have developed several new incontinence medications. Sales of these medications were predicted to measure billions of dollars in 2004. These drugs are useful in treating urge incontinence, but they can have distressing side effects that limit their use, and compliance is poor. Some patients may notice an immediate effect with medical therapy, whereas in others an effect may not be seen for approximately four weeks. Incontinence may also recur after treatment. The disadvantage of medication such as Oxybutynin, Detrol® by Pharmacia & Upjohn (now Pfizer), Ditropan XL (J&J), is the unwanted side effects. Side effects such as dry mouth, nose, and throat, dizziness, drowsiness, and confusion, decreased sweating and skin rash, nausea and constipation, eye pain, and rapid heartbeat.

Surgical implants range from nerve stimulation to mid-urethral slings, injection of bulking agents (collagen, etc.) under the bladder neck to provide support, balloons under the bladder neck to provide support, and female urethral inserts. There are nearly 200 procedures for incontinence. Most of these procedures are designed to restore the bladder neck and urethra to their anatomically correct positions in patients with stress incontinence. The American Urological Association suggests that surgery should actually be considered as initial therapy for women with severe stress incontinence. It is an effective and safe alternative when conservative treatments fail. Potential complications of all procedures include obstruction of the outlet from the bladder, causing difficulty in urination and irritation. Another problem with these implants include the fact that bulking agents such as collagen lose their effect and need to be continually reapplied. Some surgical methods such as slings only work well in females. One prior art device includes a prosthetic bladder requiring a vent through the body of the patient. The vent creates problems related to contamination and leakage and the device is only useful for patients whose bladder must be removed such as due to cancer. Other current surgical methods offer a solution that is only temporary.

Urinary incontinence affects the quality of life for all those who are afflicted with it. The current methods of treatment do not provide adequate remedies or treatments for urinary incontinence.

SUMMARY OF THE INVENTION

The present invention overcomes at least one disadvantage identified in the prior art by providing a urinary bladder valve assembly adapted for implantation into a male or female patient having a natural bladder, urethra, and an abdominal wall, the urinary bladder valve assembly comprising: a housing adapted to be secured at least to the bladder; a valve positioned within the housing and moveable between an open and a closed position; a first port having a first end attached to the housing and a second end extending from the housing a sufficient predetermined length to reach through the abdominal wall; a valve actuator adapted to open and close the valve.

Additional advantages are provided by a method of treating urinary incontinence in a male or female patient having a natural bladder comprising the steps of: providing a urinary bladder valve assembly comprising a housing, a valve positioned within the housing and moveable between an open and a closed position, at least one port having a first end attached to the housing and a second end extending from the housing, and a valve actuator adapted to open and close the valve; surgically cutting an opening into the natural bladder of the patient; attaching at least a part of the housing of the urinary bladder valve assembly to the natural bladder; and closing the opening in the natural bladder such that the at least one port of the urinary bladder valve assembly extends through the abdominal wall of the patient; and selectively opening and closing the valve by using the valve actuator.

Additional advantages are also provided by a method of performing a medical procedure on a male or female patient comprising the steps of: providing a urinary bladder valve assembly at least partially attached to the natural bladder of the patient, the urinary bladder valve assembly having at least one port having a first end accessible to the interior of the natural bladder and a second end extending through the abdominal wall of the patient; inserting at least one object through the port to perform at least one procedure from the group consisting of: (a) repair and maintenance of the valve, (b) inspection of the urinary tract and other parts of the body, (c) treatment of the urinary tract and other organs, (d) insertion of devices for performing one or more procedures such as endoscopic, laproscopic, cytoscopic, bioscopic, radioscopic, cell transplant, chemotherapy, x-ray, sonogram, drug delivery or medicinal applications, (e) removal of tissue such as bone, cartilage, kidney stones, plaque, sediments, calculi, arteries, veins, fat, or removal of gas or fluids, (f) transplanting tissue, (g) implanting stem cells, (h) modification of the genome, and (i) insertion of temporary and permanent medical devices into the port and into the body such as vascular stents, catheters, hemostats, temporary bladder liners to allow healing of the natural bladder due to interstitial cystitis.

These and other advantages will be apparent upon a review of the detailed description of the present invention.

DETAILED DESCRIPTION OF THE INVENTION

An embodiment of the apparatus 10 for repairing urinary incontinence is illustrated in various views in FIGS. 1 and 3-7 and is generally referred to herein as a urinary bladder valve assembly 10. The urinary bladder valve assembly 10 comprises a housing 20 adapted to be secured at least to the natural bladder of a male or female patient, a valve 30 positioned within the housing 20 and moveable between an open and a closed position, a first port 56 having a first end attached to the housing 20 and a second end extending from the housing 20 a sufficient predetermined length to reach through the abdominal wall of the patient, and a valve actuator 40 (best seen in a cross-section in FIGS. 3 and 4) at least partially positioned in the first port 56 and adapted to open and close the valve 30. In addition, the urinary bladder valve assembly 10 may further comprise a second port 60 having a first end attached to the housing 20 and a second end extending from the housing 20 a sufficient predetermined length to reach through the abdominal wall of the patient. The second ends of the ports 56, 60 are sealed by sealing devices 58, 62 in the form of screws, caps, plugs, or any other suitable device for preventing fluid flow through the ports 56, 60.

Figure 3:
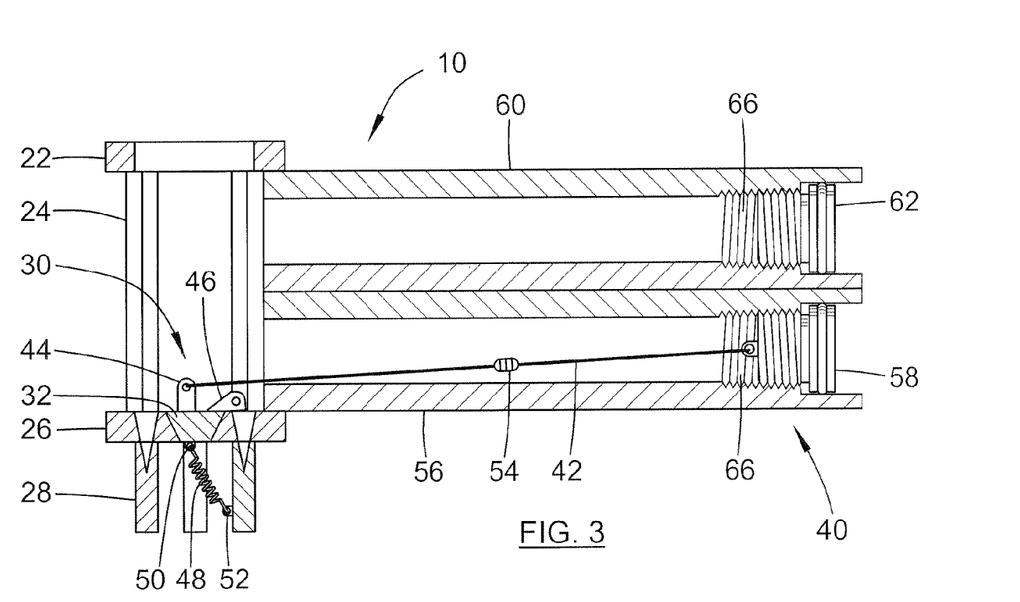
FIG. 3 is a cross sectional view of the urinary bladder valve assembly of FIG. 1 shown with the valve in a closed position.

The housing 20 comprises a cage-like structure having a top portion 22, a bottom portion 26 and a midsection 24 therebetween formed as a plurality of legs 24 that span between the top portion 22 to the bottom portion 26. The legs 24 are secured to the top portion 22 and to the bottom portion 26 by screws 70. A second plurality of legs 28 are shown extending from the bottom portion 26 and attached to the bottom portion 26 by screws 70. Referring now to FIG. 3, the valve 30 comprises a stopper 32 covering an aperture 34 through the bottom portion 26 of the housing. The valve actuator 40 comprises a linkage mechanism including a screw 58 mating internal threads 66 of the first port 56 and generally positioned near the second end of the first port 56. The screw 58 is attached to a cable 42 which in turn is attached to the stopper 32 of valve 30 to provide operation of the valve 30 as discussed in detail below. As the urinary bladder valve assembly 10 is used with a natural bladder, no venting is necessary, however, a vent could be added for if required for any reason.

Figure 1:
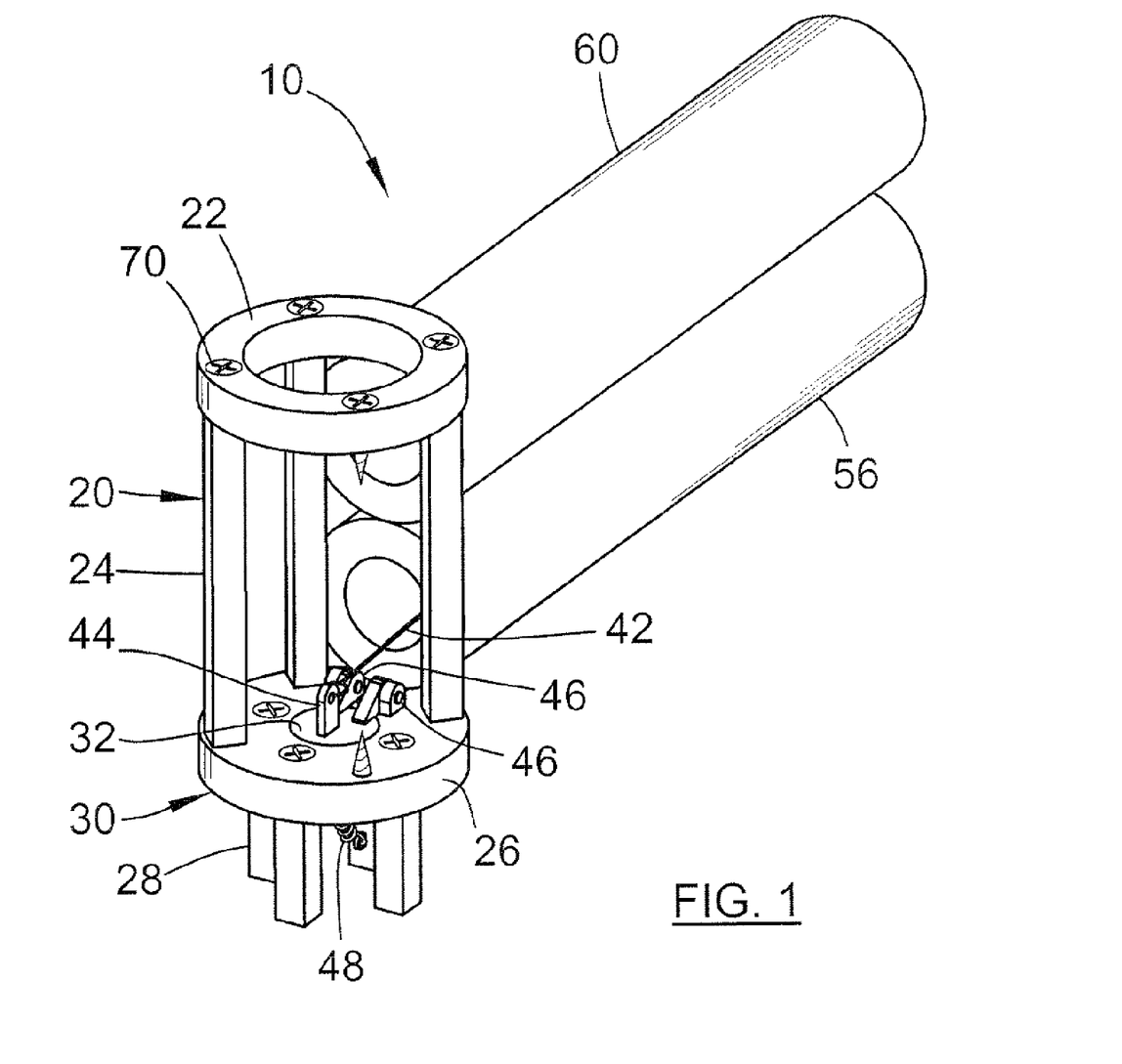
FIG. 1 is a perspective view of an embodiment of the urinary bladder valve assembly of the present invention.
Figure 2A:
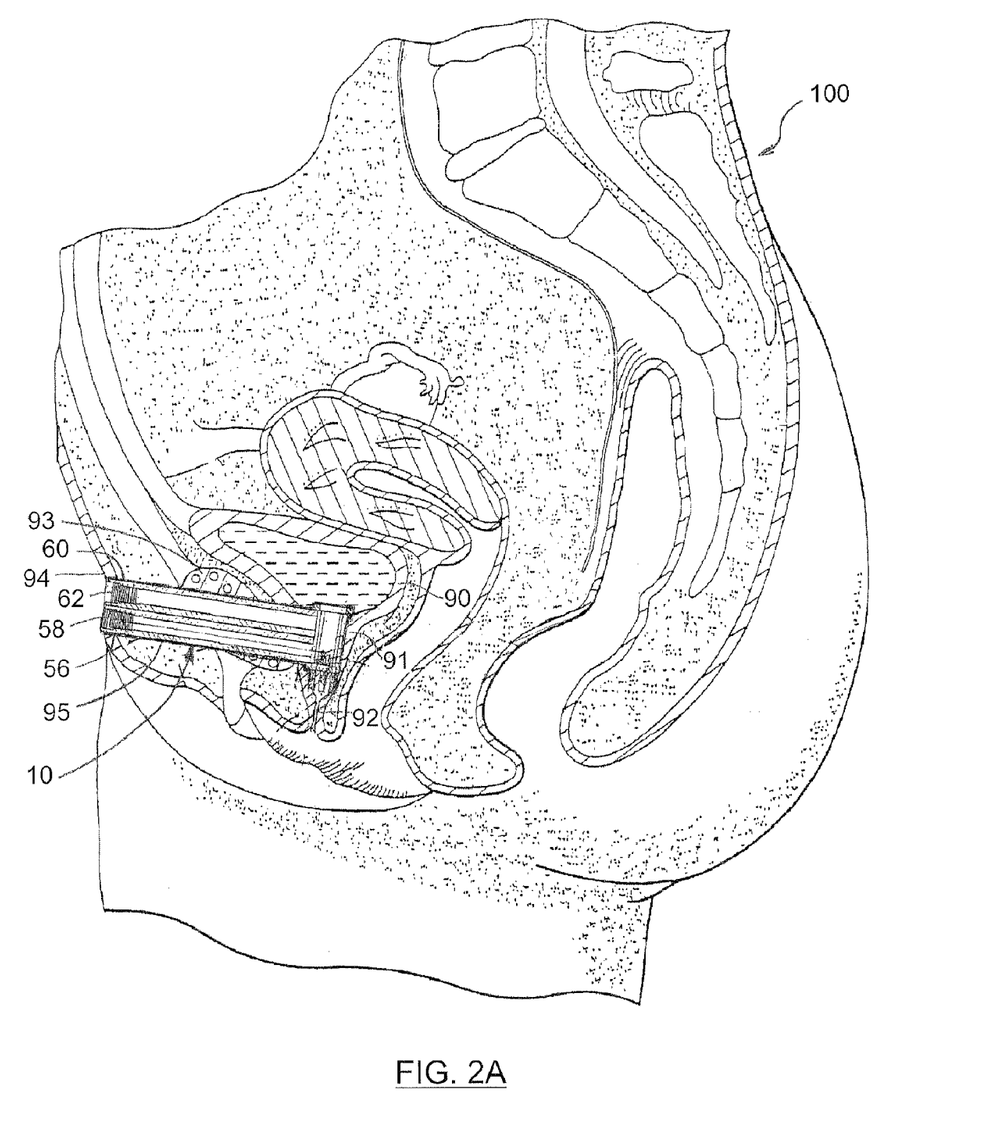
FIG. 2A is a cross-sectional view of the placement of the urinary bladder valve assembly of FIG. 1 shown implanted in the female human anatomy.
Figure 2B:
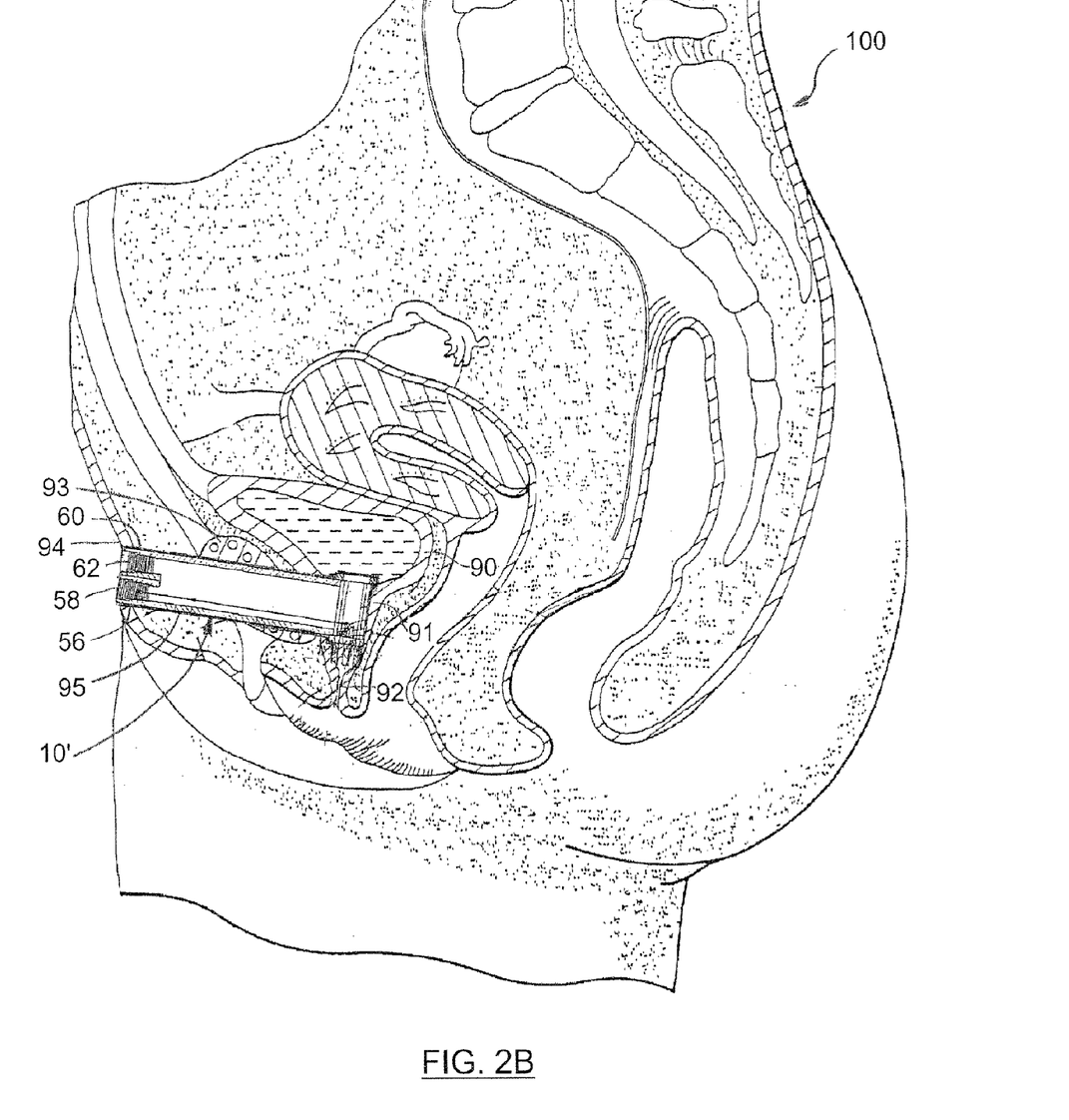
FIG. 2B is a cross-sectional view of the placement of a second embodiment of the urinary bladder valve assembly of the present invention shown implanted in the female human anatomy.

The physical dimensions and construction of the urinary bladder valve assembly 10 is selected by the physician based on the sex of the patient as well as other anatomical and medical considerations. The anatomical placement of the urinary bladder valve assembly 10 is illustrated in FIG. 2A. The anatomical placement of a second embodiment of the urinary bladder valve assembly 10' is illustrated in FIG. 2B. The second embodiment of the urinary bladder valve assembly 10' comprises a combined first port 56 and second port 60 at a location inward of the sealing devices 58, 62 to provide more room when accessing the body as discussed in greater detail below. The urinary bladder valve assembly 10' is also shown wrapped by a biocompatible material such as Selastic® membrane 95 or the like in order to prevent urethral erosion by keeping the urine away from body tissue. The different sizes of the housing 20 of the urinary bladder valve assembly 10 may be provided so that the doctor can select the optimal fit with the individual patient. The housing 20 is positioned to securely anchor the top portion 22 of the housing 20 into place at the top of the bladder neck 91 otherwise known as the trigone region of the natural bladder 90. The position of the top ring 22 may be low or high in the trigone region depending upon the individual's anatomy. The top ring 22 may be circular in shape, triangular in shape, or any other geometry depending upon the shape and anatomical condition of the bladder neck 91. The bottom portion 26 of the housing 20 includes the valve 30. The bottom portion 26 can be attached to the bottom of the bladder neck 91 or within the urethra 92 by stitching into place using fasteners which include biodegradable sutures, staples, stitching, adhesives, or other means for fastening. The bottom portion 26 and top portion 22 of the housing 20 should be attached so as to facilitate integration with the surrounding areas, and to provide optimal functioning of the valve 30. The top portion 22 of the housing 20 is orientated anterior to the bottom ring 26 of the housing 20 when implanted in the body of the patient. The bottom legs 28 may extend from the bottom portion 26 and used to secure the device 10 into the urethra 92. The bottom legs 28 may be extended into the urethra 92 and act to keep the end of the urethra 92 open. In another embodiment, the bottom legs 28 may extend around the exterior of the end of the urethra 92 and the urethra 92 secured to the legs 28. In some instances, biocompatible material may be inserted between the housing and the urethra wherein the biocompatible material provides a tubular extension connector to the urethra such that when the valve 30 is in the open position, urine may travel from the natural bladder, through the valve, through the biocompatible material and into the urethra. Regardless of the attachment of the urethra 92, the urinary bladder valve assembly 10 provides a path from the natural bladder 90 to the urethra 92, with the valve 30 providing an obstruction in the path to prevent fluid from entering the urethra 92 unless the valve 30 is opened.

The middle region 24 of the housing 20 between the top ring 22 and bottom ring 26 are shown as legs 24 however, this section can be made as a metal stent-like region (not shown) or even a cylindrical tube (not shown) to support the region in between the top ring 22 and bottom ring 26. In the first embodiment, the legs 24 may be constructed out of the same material as the top ring 22 and bottom ring 26. The structure of the middle region 24 will depend upon the amount of support needed to keep the housing securely in place and intact. The middle region 24 may also be used to secure the urinary bladder valve assembly 10 to the natural bladder 90 and/or urethra 92 with by stitching into place using fasteners which include biodegradable sutures, staples, stitching, adhesives, or other means for fastening.

Referring to FIGS. 2A and 2B, the ports 56, 60 extend from the housing 20 at a first end, through the natural bladder 90, through the pubic symphysis 93, and through the abdominal wall 94 of the patient 100. The pubic symphysis 93 is the midline cartilaginous joint uniting the superior rami of the left and right pubic bones. As the pubic symphysis 93 is a cartilage material, it can be slit or drilled to provide a harness for the ports 56, 60. The cartilage material will stretch and grow around the ports 56, 60 to repair any gaps provided by the operation. Although not shown, it is also contemplated that the ports may be anchored or otherwise attached to the pubic symphysis 93 using fasteners or the like. The placement of the ports 56, 60 in this location allows the patient 100 to have easy access to the actuator 40, minimizes the noticeability of the ports 56, 60 as they are generally below the waistline of clothing, and high enough as to not prevent sexual activity of the patient. In addition, the port location is low enough on the body that if the patient gains weight, the weight will generally be gained above the ports 56,60. If for any reason the port length does become to short, i.e. pregnancy or severe weight gain, the ports can be extended with removable extender tubes (not shown).

Although shown in FIGS. 2A and 2B implanted in a female, the urinary bladder valve assembly 10' can be used in the male anatomy as well. Modifications to the size, shape, and orientation of the urinary bladder valve assembly 10' may be needed to accommodate the prostate but the general concept is the same as shown in FIGS. 2A and 2B. It is also contemplated that the prostate be removed to better accommodate the urinary bladder valve assembly 10'. In some cancerous patients, for example, the bladder neck may have been removed. In such cases the urinary bladder valve assembly 10 may be attached to the bottom of the bladder.

Referring again to FIGS. 1 and 3, the housing 20 is shown as constructed using screws 70, any suitable construction is contemplated, including a housing formed monolithically. It is contemplated that housing 20 can be comprised of stainless steel (SS316L), Nitinol (shape memory alloy), carbon fiber or any other biocompatible, flexible material to provide support for the urinary bladder valve assembly's main features. In one embodiment, the housing 20 may be constructed from a metal with a flexible polymer coating, and in another embodiment the housing 20 may be constructed from a polymer molded into an optimized shape. The portions of the housing 20 exposed to urine must be composed of a material resistant to uric acid. As discussed in relation to FIGS. 2A and 2B, it is further contemplated that a Selastic® membrane 95 manufactured by Dow Corning or any other biocompatible material such as Gore-Tex® by W. L. Gore and Dacron® by DuPont, or other materials such as polyurethane, polydimethylsiloxane, cellulose, and other silicone polymer membranes, can be applied over the housing 20 and also may be used to create the housing 20. In addition to preventing urethral erosion from contact of tissue with urine, the coating 95 over the housing 20 may create a more stable, stronger frame for the device, which integrates into the body, may decrease healing time, and decrease infection. The housing 20 may have a coating of a drug delivery membrane. A drug coating may provide delivery of drugs over a period of time and may allow for faster healing and integration with a lower rate of infection.

Figure 4:
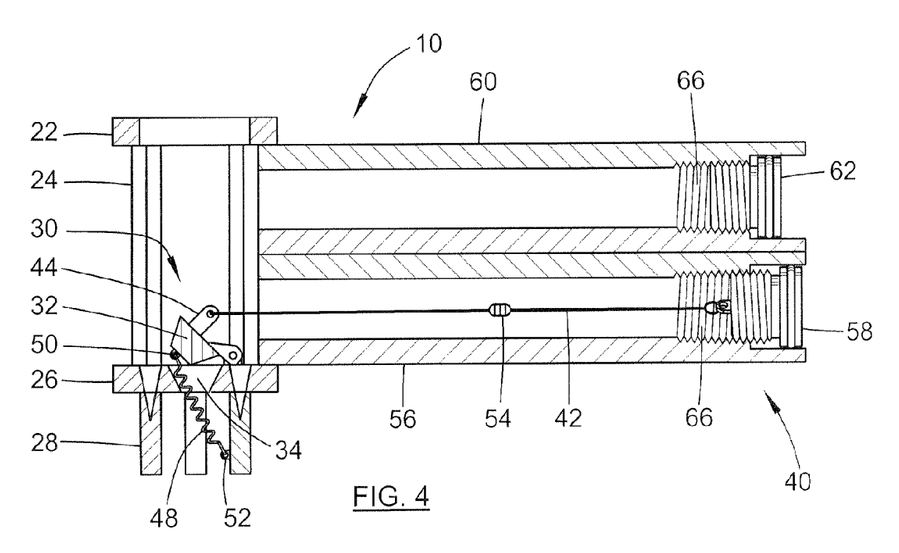
FIG. 4 is cross sectional view of the urinary bladder valve assembly of FIG. 1 shown with the valve in an open position.
Figure 5:
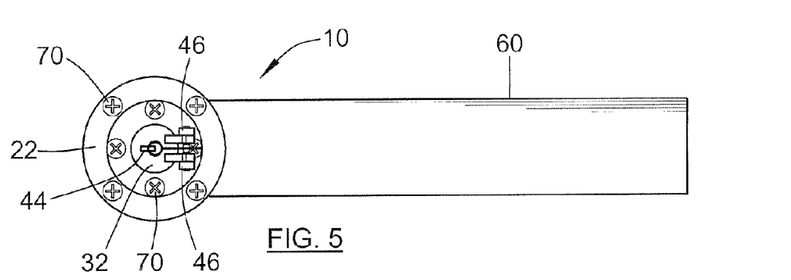
FIG. 5 is a top view of the urinary bladder valve assembly of FIG. 1.

After the device 10 is attached to the bladder, the patient or care-giver may operate the device to control the flow of urine. FIG. 3 and FIG. 4 illustrate the mechanical activation of the valve which allows the individual to control "on-demand" urination wherein FIG. 3 depicts the valve closed condition and FIG. 4 depicts the valve open condition. The valve 30 may be positioned between the top ring 22 and the bottom ring 26 of the housing 20 or may be connected or attached to the bottom ring 26 as in the shown embodiment. The valve 30 is positioned anterior of the opening between the natural bladder and urethra, and anterior to the port tubes 56, 60. The valve 30 may comprise of a stopper 32 such as a flap, ball, stop, or any other valve component to act as the stopper 32. The valve 30 may be held in place by a mechanism such as a spring 48 held in place by a top anchor 50 and a bottom anchor 52. In the closed position the valve 30 contains urine in the natural bladder. The spring 48 may keep the valve closed and stable within the housing 20. The access port 60 comprises internal threads 66 and cap in the form a head of screw fastener 62 having a seal to prevent fluid flow through the screw cap 62. The access port tube 60 may be opened by removing the screw fastener 62 using an Allen head key or the like. If the valve 30 or actuator 40 is not functioning properly, the access port tube 60 can be used as a urinary diversion to drain urine or a temporary catheter can be inserted into the access port tube 60. In the open position, the valve 30 opens aperture 34 forming a throughway passage 34 from the natural bladder and into the urethra.

Figure 6:
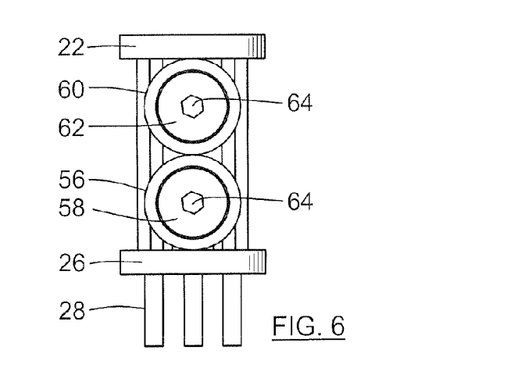
FIG. 6 is a port end view of the urinary bladder valve assembly of FIG. 1.

The valve activator 40 comprises a linkage mechanism including a screw 58 mating internal threads 66 of the first port 56 and generally positioned near the second end of the first port 56. The screw 58 is attached to a cable 42 which in turn is attached to a cable attachment boss 44 on the stopper 32 of valve 30. A swivel 54 may also be provided to keep the cable from twisting and knotting up. The valve 30 may be activated by turning the screw 56. The screw 56 may be rotated using an Allen key (not shown) inserted into the end of the screw head 64 and turning the screw 64 counter-clockwise as best shown in FIG. 6. Referring back to FIG. 4, the rotation of the screw 64 causes the screw 64 to translate within the port tube 56 moving the cable 42 away from the housing 20. The cable 42 causes the valve 30 to open by pulling on the stopper 32 and forcing the stopper 32 to rotate about its hinges 46 up and away from the throughway passage 34 between the natural bladder and urethra, resulting in the release of the urine. When the natural bladder is emptied, the screw 56 is rotated using the Allen key in a clockwise direction causing the screw 64 to translate within the port tube 56 moving the cable 42 back toward the housing 20. The release of tension on the cable 42 allows the biasing force of the spring 42 to rotate the stopper 32 back into sealing engagement with the throughway passage 34. The tension from the spring 42 is sufficient to hold the valve 30 closed when the cable 42 is released. The accumulation of urine in the natural bladder will also create a force tending to keep the stopper 32 sealingly engaged with the throughway passage 34.

The valve and operation of the valve is not intended to be limited to the embodiment shown and it is contemplated that any known valve 30 and actuator 40 may be used within the scope of the present invention. In one contemplated embodiment the valve 30 may comprise of a rotatable shaft extending through the port with a half ball end such that the ball portion of the end engages the throughway to close the valve. The valve is actuated by rotation of the shaft such that the non ball portion of the end allows the urine to pass through. The valve may also comprise of any other alternative embodiment that functions as a one way valve.

As mentioned above, the present invention includes at least one port tube 56, 60 extending from the housing to through the abdominal wall of the patient. In the embodiment shown, there are two ports 56, 60 wherein the first port 56 is used for the actuator 40 and the second port tube 60 is an access port. The access port tube 60 provides a "non-invasive" and painless method of repairing or replacing the valve 30 or actuator 40 without requiring the device 10 to be removed from the body.

With removal of the actuator 40 within port 56 or any secondary port, such as access port tube 60, there is provided an entry port into the natural bladder for the physician. The access port 60 provides improvement over the current noninvasive and invasive surgically techniques or methods. The non-invasive attributes of the access port tube 60 may include but are not limited to urinary diversion, repair and maintenance of valve, inspection and treating of urinary tract with cytoscope or other urological and medical devices. The access port tube 60 may be used for traditional urological studies, flushing or cleansing of the urinary tract, providing antibiotics or medication directly to wounds or infection, removing kidney stones and calculi, biopsy, treating the prostate, and radiation therapy applied directly to the specific tissue; interstitial cystitis, a chronic inflammatory condition of the bladder, can be diagnosed and treated through the access port by cytoscopic methods.

The access port tube 60 also provides an entry port into the body for the physician wherein the physician can cut through the natural bladder wall, or any other structure such as the wall of the housing 20, to access the majority of the body. The wall can be cauterized or stitched closed when the procedure is complete. The procedures may involve inserting at least one object through the port to perform a medical procedure or observation. These procedures may include endoscopic, laproscopic, cytoscopic, bioscopic, radioscopic, cell transplant, chemotherapy, x-ray, sonogram, drug delivery or medicinal applications, and removal of tissue, or fluids through the port. Additional procedures contemplated include transplanting tissue, implanting stem cells, and modification of the genome.

The present invention discloses a remedy focused on permanent rehabilitation, and providing a higher quality of life for the individual. Before the implanted device, the patient must rely on the current treatments mentioned above with the many disadvantages. After the implanted device, the patient can operate his or her own natural bladder in the way a normal, healthy bladder operates before urinary incontinence. The present device may act to simulate this normal urination process which would include complete emptying of the natural bladder by way of a mechanically actuated valve. The patient may function normally and engage in activities without worrying about changing absorbent pads, catheters, or fear of overflow and wetting. In addition, the present invention may provide an alternate means of treatment superior to any current method of treatment or cure. The present invention has the ability to regulate urination and may provide a port to other areas of the body as well. The port disclosed in the present invention may allow access to the natural bladder, ureters, kidneys, and other areas of the abdomen and body cavity as discussed above.

The urinary bladder valve of the present invention cures incontinence and provides a "trap-door" to the natural bladder and the rest of the body. Although a list of devices and procedures have been listed that are now possible for use through the ports of the present invention, it is contemplated that this innovation will enable new medical procedures and new devices, instruments and tools to be developed and utilized.

While this invention has been described with reference to preferred embodiments thereof, it shall be understood that such description is by way of illustration and not by way of limitation. Accordingly, the scope and content of the present invention are to be defined only by the terms of the appended claims.

What is claimed is:

1. A urinary bladder valve assembly adapted for implantation into a male or female patient having a natural bladder, urethra and an abdominal wall, the urinary bladder valve assembly comprising:

a housing adapted to be secured to at least to a bottom of the natural bladder and a top end of the urethra;

a valve positioned within the housing and moveable between an open position wherein urine is able to flow from the bladder through the valve to the urethra and a closed position wherein urine is prevented from flowing from the bladder to the urethra;

wherein the valve comprises a stop valve and the stop valve is biased in the closed position by a spring;

a first port having a first end attached transversely to the housing and a second end extending from the housing a sufficient predetermined length to reach through the abdominal wall;

a valve actuator comprising a cable attached at a first end to the valve and a second end attached to an actuator screw threadably positioned within the first port, wherein rotation of the actuator screw in a first direction causes the valve to move from a closed position to an open position and rotation of the actuator screw in a second direction allows the valve to move from an open position to a closed position; wherein the valve actuator is at least partially positioned in the first port; and a removable sealing device positioned to prevent fluid flow through the first port.

2. The urinary bladder valve assembly of claim 1 further comprising;

a second port having a first end attached to the housing and a second end extending transversely from the housing a sufficient predetermined length to reach through the abdominal wall.

3. The urinary bladder valve assembly of claim 2 further comprising: a removable sealing device positioned to prevent fluid flow through the second port.

4. The urinary bladder valve assembly of claim 1, wherein the valve comprises a flow control valve.

5. A method of treating urinary incontinence in a male or female patient having a natural bladder comprising the steps of:

providing a urinary bladder valve assembly comprising a housing, a valve positioned between a first end of the housing and a second end of the housing, the valve moveable between an open and a closed position, at least one port having a first end attached to the housing and a second end extending transversely from the housing, and a valve actuator adapted to open and close the valve;

surgically cutting an opening into the natural bladder of the patient;

attaching the first end of the housing of the urinary bladder valve assembly to the natural bladder and attaching the second end of the housing to the urethra;

wherein the at least one port of the urinary bladder valve assembly extends through the abdominal wall of the patient;

surgically closing the opening into the natural bladder and urethra of the patient; and selectively opening and closing the valve by using the valve actuator wherein urine flows from the bladder through the valve and through the urethra when the valve is in the open position and urine is prevented from flowing from the bladder to the urethra when the valve is in the closed position.

6. The method of claim 5 further comprising the steps of: attaching or anchoring the at least one port to the pubis symphysis.

7. The method of claim 5 wherein the step of selectively opening and closing the valve by using the valve actuator is accomplished by turning a screw positioned in the at least one port such that a cable attached to the screw is translated and moves the valve to the open position, and rotating the screw in an opposite direction to translate the cable to allow the valve to move to the closed position.

8. The method of claim 5, wherein the step of attaching a first end of the housing of the urinary bladder valve assembly to the natural bladder and attaching a second end of the housing of the urinary bladder valve assemble to the urethra is accomplished using a fastener.

9. The method of claim 5 further comprising the step of covering at least a portion of the urinary bladder valve assembly with a biocompatible material.

10. The method of claim 5 further comprising the step of inserting a biocompatible material between the housing and the urethra wherein the biocompatible material provides a tubular extension connector to the urethra such that when the valve is in the open position, urine may travel from the natural bladder, though the valve, through the biocompatible material and into the urethra.

11. The method of claim 5 further comprises the steps of:
opening the at least one port by removing a sealing device from the at least one port;
repairing or maintaining the urinary bladder valve assembly by inserting one or more devices through the at least one port.

12. The method of claim 5 further comprising the steps of:
opening the at least one port by removing a sealing device from the at least one port;
inserting at least one object into the at least one port in order to observe or treat the natural bladder or other parts of the body.

13. The method of claim 10 further comprising the step of:
inserting at least one object through the port to perform at least one procedure from the group consisting of:
(a) inspection of the urinary tract and other parts of the body,
(b) treatment of the urinary tract and other organs,
(c) insertion of devices for performing endoscopic, laproscopic, bioscopic, radioscopic, cell transplant, chemotherapy, x-ray, sonogram, and drug delivery,
(d) removal of tissue, bone, cartilage, kidney stones, plaque, sediments, calculi, arteries, veins, fat, gas or fluids,
(e) transplanting tissue,
(f) implanting stem cells,
(g) modification of the genome, and
(h) insertion of temporary and permanent medical devices into the port and into the body; the medical devices selected from the group comprising vascular stents, catheters, hemostats, and temporary bladder liners to allow healing of the natural bladder due to interstitial cystitis.

* * * * *